United States Patent [19]
Galley et al.

[11] Patent Number: 5,817,298
[45] Date of Patent: Oct. 6, 1998

[54] TITANIUM DIOXIDE SUNSCREENS

[75] Inventors: Edward Galley, Nottinghamshire; Nicola Anne Elsom, Leicestershire, both of England

[73] Assignee: The Boots Company PLC, Nottingham, England

[21] Appl. No.: 687,891

[22] PCT Filed: Nov. 27, 1989

[86] PCT No.: PCT/EP89/01438

§ 371 Date: May 30, 1991

§ 102(e) Date: May 30, 1991

[87] PCT Pub. No.: WO90/06103

PCT Pub. Date: Jun. 14, 1990

[30] Foreign Application Priority Data

Nov. 30, 1988 [GB] United Kingdom .................. 8827968

[51] Int. Cl.$^6$ .............................. A61K 7/42; A61K 7/00
[52] U.S. Cl. ........................... 424/59; 424/60; 424/400; 424/401
[58] Field of Search ............... 424/59, 406, 401

[56] References Cited

U.S. PATENT DOCUMENTS

| | | | |
|---|---|---|---|
| 3,017,283 | 1/1962 | Bennetch et al. ................. | 106/304 |
| 4,305,853 | 12/1981 | Kronstein et al. ................ | 260/22 A |
| 4,379,136 | 4/1983 | Mochida ........................... | 424/65 |
| 4,520,153 | 5/1985 | Kronstein et al. ................ | 524/145 |
| 4,622,074 | 11/1986 | Miyoshi et al. .................. | 106/308 |
| 4,857,308 | 8/1989 | Fukasawa et al. ................ | 424/63 |
| 4,938,960 | 7/1990 | Ismail .............................. | 424/195 |
| 4,980,157 | 12/1990 | Mercado et al. .................. | 424/69 |
| 5,024,827 | 6/1991 | Jones et al. ...................... | 423/610 |
| 5,028,417 | 7/1991 | Bhat et al. ....................... | 514/847 |

FOREIGN PATENT DOCUMENTS

| | | | |
|---|---|---|---|
| 2113116 | 8/1983 | United Kingdom .................. | 424/59 |
| 2184356 | 6/1987 | United Kingdom .................. | 424/59 |
| 2217987 | 11/1989 | United Kingdom .................. | 424/59 |

OTHER PUBLICATIONS

Derwent Abstract No. 87–159761/23 –Asada Seifun KK.
Derwent Abstract No. 85–305541/49 –Y.G. Miyoshi Kasei.
Derwent Abstract No. 49912K/12 –Shiseido KK.
Derwent Abstract No. 84–279241/45 –Pola Kasei Kogyo KK.
Derwent Abstract No. 86–294388/45 –Tikoku Kako KK.
Seifen–Ole–Fette–Wachse 113(20), 10 Dec. 1987, Augsburg, W. Germany, pp. 765–771.
Patent Abstracts of Japan 11 (371) (C–462) (2818) 3 Dec. 1987 –Kao Corporation.
Congr. Fatipec 18th (1987), vol. 3, pp. 55–72 –Dr. H.H. Luginsland.
Fureguransu janaru (Fragrance Journal), 1987 (84),64–70 – S. Nakada & H. Konishi.
Derwent Abstract No. 86–024677/04 –Nisshon Oil Mills KK.
Derwent Abstract No. 85–160249/27 –Noronha RV.
Derwent Abstract No. 31648C/18 –Kanebo KK.
Derwent Abstract No. 74115B/41 –Miyazoe T.
Derwent Abstract No. 81654V/47 Nikko Chems. KK.
Farbe & Lack, vol. 94(3), 1988 –Dr. U. Gesenhues.

*Primary Examiner*—Shelley A. Dodson

[57] ABSTRACT

Titanium dioxide particles having a mean primary particle size of less than 100 nm, each of said particles being substantially coated with phospholipid are disclosed. The phospholipid is preferably selected from phosphatidyl cholines, phosphatidyl ethanolamines, phosphatidyl serines, phosphatidyl inositols and mixtures thereof, in particular lecithin. Phospholipid-coated titanium dioxide particles may be incorporated into oil-in-water and water-in-oil emulsions to provide novel sunscreen compositions with excellent ultraviolet screening efficiency, long term stability and water-resistant properties.

24 Claims, No Drawings

TITANIUM DIOXIDE SUNSCREENS

The present invention relates to coated titanium dioxide particles for use in sunscreen compositions. The term "sunscreen" is used herein to encompass tanning lotions, sunscreens and sunblockers which are intended for topical application to provide protection against the sun's rays or other sources of ultraviolet (UV) radiation.

Conventional sunscreen compositions have been prepared either as oil-in-water or water-in-oil emulsions containing organic sunscreen agents which could be formulated equally successfully in either of the above emulsion systems. More recently sunscreen compositions have been proposed which contain, as the sunscreening agent, titanium dioxide.

Titanium dioxide particles have a tendency to agglomerate and this effect reduces their efficacy as UV screening agents and increases their whiteness on the skin (opacity). Agglomeration also results in the breakdown of emulsions containing such particles and adversely affects their stability during prolonged storage. It is known to coat titanium dioxide particles with compounds such as aluminium stearate and aluminium oxide in order to minimise light-induced reduction and to increase the hydrophobicity of the particles, thereby aiding their dispersion. However, even stearate-coated titanium dioxide particles do not disperse entirely effectively in lipophilic phases such as silicone but tend to form clumps, presumably as a result of interaction between the stearate chains of adjacent particles. The present invention stems from the applicants discovery that coating titanium dioxide particles with phospholipid reduces their tendency to clump and enables the particles to be more effectively dispersed.

The present invention provides titanium dioxide particles having a mean primary particle size of less than 100 nm, each of said particles being substantially coated with phospholipid. It will be understood that the phrases "titanium dioxide particles substantially coated with phospholipid" and "phospholipid-coated titanium dioxide" as used herein describe particles of titanium dioxide to which a substantial number of phospholipid molecules are bonded. The bonding of phospholipid molecules to titanium dioxide particles may occur during an initial coating procedure or may arise spontaneously in situ within the oil phase of a sunscreen composition in which both titanium dioxide and phospholipid are present.

Phospholipids of use in the present invention may be naturally occurring or synthetic phospholipids or mixtures thereof., Naturally occurring phospholipids include, for example, phosphatidyl cholines, phosphatidyl ethanolamines, phosphatidyl serines, phosphatidyl inositols, diphosphatidyl glycerols and sphingomyelins. These natural phospholipids may be prepared from, for example, mammalian brain or liver tissue, egg yolk, soybean or bacterial cell membranes. Numerous synthetic phospholipids are also commercially available and may, for example, be derived from naturally occurring oils such as rapeseed oil which have been partly or fully hydrogenated, selectively esterified to a glycerol backbone and phosphorylated to form specific phosphatidates or mixtures thereof. Other synthetic phospholipids may be derived from naturally occurring phospholipids which have been modified, for example by hydroxylation or ethoxylation.

Phospholipids carry one or two, more usually two $C_{8-32}$ alkyl groups bound to a polar phosphorylated alcohol head-group. The alkyl groups may be straight or branched chain, saturated or unsaturated, and may be optionally substituted, for example, by one or more hydroxyl groups. Preferably the phospholipids of use in the present invention carry two $C_{8-32}$ alkyl groups, more particularly $C_{12-24}$ alkyl groups. Most preferred phospholipids are phosphatidyl cholines, phosphatidyl ethanolamines, phosphatidyl serines and phosphatidyl inositols and mixtures thereof. A particularly suitable type of phospholipid for coating titanium dioxide particles according to the present invention is phosphatidyl choline. Mixtures of phosphatidyl cholines are readily available as lecithins derived from plant or animal tissues. One particularly preferred lecithin, derived from soybean, contains a mixture of β-phosphatidyl cholines comprising diglycerides of stearic, palmitic and oleic acids and is available commercially from Central Soya Co. under the trade designation Lecithin P Centrolex.

The ratio of phospholipid to titanium dioxide on a weight:weight basis is generally in the range of 0.1:100 to 5:100 particularly 0.2:100 to 12:700. More particularly the phospholipid represents 0.25 to 10%, preferably 0.5 to 5% of the total weight of the titanium dioxide particles according to the invention. Most preferably the phospholipid represents 0.5 to 4%, especially 1 to 2%, for example about 1.5% of the total weight of titanium dioxide particles.

The titanium dioxide preferably has a mean primary particle size of between 1 and 100 nm, more preferably between 5 and 50 nm, most preferably between 10 and 35 nm. Titanium dioxide of the above mean primary particle size is usually referred to as "microfine". The titanium dioxide may have an anatase, rutile or amorphous structure. The particles may be uncoated or may be provided with a coating of, for example, an aluminium compound such as aluminium oxide, aluminium stearate or aluminium laurate. Microfine titanium dioxide is available from Degussa under the trade designation P25 and from Teikoku Kako Co Ltd under the trade designation MT150W, MT600B or MT500B. Titanium dioxide coated with aluminium stearate is available from Teikoku Kako Co Ltd under the trade designation MT100T and titanium dioxide coated with aluminium oxide is available from Miyoshi under the trade designation UFTR.

The particles of the present invention may be prepared by mixing titanium dioxide particles with a phospholipid which is fluid at the temperatures attained during mixing. Advantageously the phospholipid is pre-mixed with a cosmetically acceptable carrier such as a fatty ester, for example isopropyl palmitate, unsaturated fatty alcohol, paraffin or low molecular weight triglyceride. The ratio of phospholipid to carrier may vary, for example where the carrier is a phospholipid solvent the ratio of phospholipid to solvent may vary according to the solubility of the phospholipid in the solvent used, but is typically in the range of 1:10 to 1:1. By way of example, lecithin may be dissolved in twice its weight of isopropyl palmitate by heating to about 85° C. This solution may then be slowly added to titanium dioxide particles using a high speed powder blender or granulation mixer, for example a Papenmeiyer or Diosna mixer, in a ratio of, for example, 4.5 parts lecithin solution to 95.5 parts titanium dioxide. Preferably the lecithin solution is sprayed onto the titanium dioxide during mixing. Finally the mixture may be powder milled, for example using a hammer mill such as a Mikropul Ducon mill, a pin mill such as a Condox mill, or a ball or bead mill. Milling is continued for sufficient time, typically for 1 to 24 hours, to produce a good dispersion, preferably in the form of a fine free-flowing powder of phospholipid-coated titanium dioxide particles according to the invention. Alternatively, a fine free-flowing powder may be very rapidly achieved using a jet mill such as an Alpine mill.

Alternatively the particles of the present invention may be prepared in situ within the oil phase of the desired composition. Advantageously the phospholipid is pre-mixed with a proportion of the oil-phase constituents of the desired composition, optionally with heating for example to 20°–80° C. The titanium dioxide may then be added directly to the phospholipid mixture to give a concentration of titanium dioxide preferably within the range 20 to 50%. The mixture is then worked with, for example, a high shear mixer such as a Torrance blender or a bowl-type mixer such as a Diosna mixer until a good dispersion is achieved, for example for ½ to 6 hours.

Phospholipid-coated titanium dioxide particles according to the present invention may be incorporated into cosmetic products in the conventional way together with conventional cosmetically acceptable carriers. The enhanced dispersibility of the particles according to the invention allows higher concentrations of titanium dioxide than were hitherto possible to be incorporated into stable fluid emulsions and dispersions. Thus the present invention provides a sunscreen composition which comprises 0.5 to 50% by weight of phospholipid-coated titanium dioxide particles as described herein, together with a cosmetically acceptable carrier. Compositions for use as sunscreen products generally contain 0.5 to 30% by weight of titanium dioxide. However, compositions containing high concentrations of phospholipid-coated titanium dioxide particles may find particular use as concentrated sunscreen compositions or so-called "master mixes" suitable for bulk storage as stable fluid emulsions or dispersions. Such compositions preferably contain 20 to 50% by weight of titanium dioxide in an oil phase dispersion.

The enhanced dispersibility of the particles according to the invention has also been demonstrated to improve the UV screening efficiency and long term stability of emulsions containing them. Furthermore, these emulsions possess excellent water-resistant properties.

Accordingly a further aspect of the present invention provides a sunscreen composition comprising a water-in-oil emulsion which comprises:

a) 0.5 to 30% by weight of titanium dioxide particles having a mean primary particle size of less than 100 nm, each of said particles being substantially coated with phospholipid;
b) 5 to 50% by weight of an oil phase;
c) 1 to 15% by weight of an emulsifier; and
d) at least 40% bv weight of an aqueous phase.

A still further aspect of the invention provides a sunscreen composition comprising an oil-in-water emulsion which comprises:

a) 0.5 to 30% by weight of titanium dioxide particles having a mean particle size of less than 100 nm, each of said particles being substantially coated with phospholipid;
b) 5 to 40% by weight of an oil phase;
c) 1 to 20% by weight of an emulsifier; and
d) at least 50% by weight of an aqueous phase.

The amount of titanium dioxide present in any particular sunscreen composition according to the present invention depends on the use for which the composition is intended. Amounts as low as 1% may be sufficient in the so-called "suntanning" products which are not intended to prevent the sun's rays reaching the skin whereas the so-called "sunblocks" which are intended to prevent substantially all of the sun's rays reaching the skin may require levels of 15 to 20%. Sunscreen compositions will more usually contain 2.5 to 15% by weight of titanium dioxide.

Other sunscreening agents may be incorporated into the compositions of the present invention. Examples of suitable further sunscreening agents include:

a) p-aminobenzoic acids, esters and derivatives thereof, for example, 2-ethylhexyl p-dimethylamino-benzoate;
b) methoxycinnamate esters such as 2-ethylhexyl p-methoxycinnamate, 2-ethoxyethyl p-methoxycinnamate or α,β-di-(p-methoxycinnamoyl)-α'-(2-ethylhexanoyl)-glycerin;
c) benzophenones such as oxybenzone;
d) dibenzoylmethanes; and
e) salicylate esters.

Any additional sunscreening agent may be present in an amount from 0.1 to 10% by weight of the composition.

The oil phase of the oil phase dispersions and the water-in-oil and oil-in-water emulsions of the present invention may comprise for example:

a) hydrocarbon oils such as paraffin or mineral oils;
b) waxes such as beeswax or paraffin wax;
c) natural oils such as sunflower oil, apricot kernel oil, shea butter or jojoba oil;
d) silicone oils such as dimethicone, cyclomethicone or cetyldimethicone;
e) fatty acid esters such as isopropyl palmitate or isopropyl myristate;
f) fatty alcohols such as cetyl alcohol or stearyl alcohol; or
g) mixtures thereof.

In preferred water-in-oil compositions of the present invention the oil phase comprises 5 to 40%, more preferably 10 to 30% by weight of the composition. In preferred oil-in-water compositions of the present invention the oil phase comprises 5 to 30%, more preferably 10 to 20% by weight of the composition.

The emulsifiers used may be any emulsifiers known in the art for use in water-in-oil or oil-in-water emulsions. It has been found that particularly effective water-in-oil and oil-in-water sunscreen compositions can be prepared by using an emulsifier or mixture of emulsifiers selected from known cosmetically acceptable emulsifiers which include:

a) sesquioleates such as sorbitan sesquioleate available commercially for example under the trade name Arlacel 83(ICI);
b) ethoxylated esters of derivatives of natural oils such as the polyethoxylated ester of hydrogenated castor oil available commercially for example under the trade name Arlacel 989(ICI);
c) silicone emulsifiers such as silicone polyols available commercially for example under the trade name ABIL WS08 (Th.Goldschmidt AG) and under the trade designation Silicone Fluid 3225C (Dow Corning);
d) fatty acid soaps such as potassium stearate;
e) ethoxylated fatty alcohols, for example the emulsifiers available commercially under the trade name Brij (ICI) and under the trade name Cithrol GMS A/S (Croda);
f) sorbitan esters, for example the emulsifiers available commercially under the trade name Crill (Croda);
g) ethoxylated sorbitan esters, for example the emulsifiers available commercially under the trade name Tween (ICI);
h) ethoxylated fatty acid esters such as ethokylated stearates, for example the emulsifiers available commercially under the trade name Myrj (ICI);

i) ethoxylated mono-, di-, and tri-glycerides, for example the emulsifier available commercially under the trade name Labrafil (Alfa Chem.);

j) ethoxylated fatty acids, for example the emulsifiers available commercially under the trade name Tefose (Alfa Chem.); and k) mixtures thereof.

The amount of emulsifier present in the water-in-oil compositions of the present invention is preferably in the range 2 to 10%. The amount of emulsifier present in the oil-in-water compositions of the present invention is preferably in the range 1 to 15%, more preferably 2 to 15%. Preferred water-in-oil emulsifiers include silicone polyols, sorbitan sesguioleates and sorbitan esters. Preferred oil-in-water emulsifiers include ethoxylated fatty acids and alcohols, ethoxylated stearates and ethoxylated triglycerides and mixtures thereof.

The compositions of the present invention may additionally comprise other components which will be well known to those skilled in the art, for example, emolients such as isopropyl myristate or triglycerides of fatty acids (e.g. lauric triglyceride or capric/caprylic triglyceride such as the triglyceride available commercially under the trade name Migliol 810 (Huls UK), moisturisers such as D-panthenol, humectants such as glycerin or 1,3-butylene glycol, antioxidants such as DL-A-tocopherylacetate or butylated hydroxytoluene, emulsion stabilising salts such as sodium chloride, sodium citrate or magnesium sulphate, film formers to assist spreading on the surface of the skin such as alkylated polyvinylpyrrolidone, preservatives such as bronopol, sodium dehydroacetate, polyhexamethylenebiguanide hydrochloride, isothiazolone or diazolidinylurea, perfumes and colouring.

The efficacy of the compositions may be measured in user tests, i.e. in vivo, or, more conveniently, in a model system disclosed by Dr M Stockdale at the Joint Symposium of the Society of Cosmetic Scientists and the Societe Francaise de Cosmetologie, held in Stratford, UK in April 1986 and subsequently published in the International Journal of Society of Cosmetic Scientists, 9, pp 85–98 (1987). Essentially, a cast of human skin is taken so that the topography of the skin is reproduced exactly. The first (negative) cast is made from silicone rubber and then a second (positive) cast is made from an ultraviolet (UV) transparent material such as Luviset CAP-X (BASF) in ethanol. Luviset CAP-X is a hair lacquer. UV light from a 900W Xenon Arc Clinical Photo-Irradiator (Applied Photophysics Ltd) is supplied via a 1 m×5 mm flexible light guide (Applied Photophysics Ltd) and passed through the second cast to give a 2 cm diameter beam on a thermopile or a UV-310 sensor coupled to a UVX Radiometer (Ultra Violet Products Inc, USA). The product to be tested is allowed to equilibrate for at least 48 hours after formulation and is then dispensed onto the second cast and spread on the surface of the cast to give an even layer of either 1.5 or 2.0 mg/cm$^2$. A cast sun protection factor can be derived by dividing (Detector reading without the product) by (Detector reading with the product). Errors referred to herein were calculated using an average obtained from a minimum of twelve measurements on separate casts.

Agglomeration of titanium dioxide particles can be determined by microscopic examination of the particles under polarised light at a magnification of, for example, ×400 or by analysis of scanning electron microscope photomicrographs. The opacity of emulsions may be estimated by trained observers by subjective visual analysis of the relative transparency of an emulsion spread onto skin. The opacity of a titanium dioxide composition is a function of the agglomeration of particles therein and thus provides an estimate of the effectiveness of the dispersion.

The invention is illustrated by the following Examples 1 to 35. Examples 14 to 33 were formulated as water-in-oil emulsions and Examples 34 and 35 were oil-in-water formulations. Examples 1 to 35 are given by way of example only. Comparative Examples A to E form no part of the present invention.

EXAMPLE 1

| | | |
|---|---|---|
| 1) | Isopropyl palmitate | 3 g |
| 2) | Lecithin (sold under the trade name P Centrolex) | 1.5 g |
| 3) | Titanium dioxide coated with aluminium stearate (sold under the trade designation MT100T) | 95.5 g |

Components 1 and 2 were mixed together and heated to 85° C. This solution was slowly added to component 3 with mixing on a high speed powder mixer (Papenmeiyer). The resulting mixture was mixed for a further 15 minutes using the Papenmeiyer. The powder was then milled twice using a hammer mill (Mikropul Ducon) to produce a fine, free-flowing powder.

EXAMPLE 2

| | | |
|---|---|---|
| 1) | Isopropyl palmitate | 6 g |
| 2) | Lecithin (soid under the trade name P Centrolex) | 3 g |
| 3) | Titanium dioxide coated with aluminium stearate (sold under the trade designation MT100T) | 91 g |

The above components were formulated as described in Example 1 to give a powder.

EXAMPLE 3

| | | |
|---|---|---|
| 1) | Isopropyl palmitate | 20 g |
| 2) | Lecithin (sold under the trade name p Centrolex) | 10 g |
| 3) | Titanium dioxide coated with aluminium stearate (sold under the trade designation MT100T) | 90 g |

The above components were formulated as described in Example 1.

EXAMPLES 4 to 13

Different types of titanium dioxide and different types of phospholipids were formulated as described in Example 1 to give the powders of Examples 4 to 13 as shown in Table 1 (Example 1 included for comparison).

TABLE 1

| Ex | TiO$_2$ Trade Designation (coating) | Average TiO$_2$ particle size/nm | Phospholipid (Source) |
|---|---|---|---|
| 1 | MT100T (Aluminium stearate) | 15 | Lecithin (Central Soya Co.) |
| 4 | MT150W (None) | 15 | Lecithin (Central Soya Co.) |

TABLE 1-continued

| Ex | TiO$_2$ Trade Designation (coating) | Average TiO$_2$ particle size/nm | Phospholipid (Source) |
|---|---|---|---|
| 5 | MT500B (None) | 35 | Lecithin (Central Soya Co.) |
| 6 | MT600B (None) | 50 | Lecithin (Central Soya Co.) |
| 7 | UFTR (Aluminium oxide) | 35 | Lecithin (Central Soya Co.) |
| 8 | MT100T (Aluminium stearate) | 15 | Phosphatidyl inositol (Sigma) |
| 9 | MT100T (Aluminium stearate) | 15 | Phosphatidyl ethanolamine (Sigma) |
| 10 | MT100T (Aluminium stearate) | 15 | Phosphatidyl serine (Sigma) |
| 11 | MT100T (Aluminium stearate) | 15 | Hydroxylated de-oiled lecithin derived from soya bean (Croda) |
| 12 | MT100T (Aluminium stearate) | 15 | Synthetic phosphatidate derived from selectively hydrogenated (iodine value = 75) rapeseed oil (Croda) |
| 13 | MT100T (Aluminium stearate) | 15 | Synthetic phosphatidate derived from fully hydrogenated soyabean oil (Croda) |

EXAMPLE 14

| | | % |
|---|---|---|
| 1) | A mixture of silicone copolyol and cyclo-methicone (sold under the trade designation Silicone Fluid 3225C) | 12.0 |
| 2) | Cyclomethicone (sold under the trade designation Silicone Fluid 345DC) | 15.0 |
| 3) | Cetyl dimethicone (sold under the trade name Abil B9801) | 5.0 |
| 4) | Sorbitan sesquioleate (sold under the trade name Ariacel 83) | 3.0 |
| 5) | Butylated hydroxytoluene | 0.05 |
| 6) | Titanium dioxide coated in accordance with Example 1 | 10.0 |
| 7) | Sodium citrate | 4.0 |
| 8) | Sodium dehydroacetate | 0.15 |
| 9) | Bronopol | 0.02 |
| 10) | Purified water | to 100 |

Components 1 to 5 were mixed together at 65°–70° C. and the titanium dioxide (component 6) dispersed into the mixture using a high shear mixer/homogeniser (Silverson). Components 7 to 10 were mixed together and then slowly added to the titanium dioxide mixture with stirring. The resulting mixture was homogenised using a high shear mixer/homogeniser to give a cream.

EXAMPLES 15 to 20

Titanium dioxide coated in accordance with Examples 2 to 7 were each formulated as described in Example 14 to give the compositions of Examples 15 to 20 respectively.

EXAMPLE 21

| | | % |
|---|---|---|
| 1) | Light liquid paraffin (sold under the trade designation WOM14) | 5.0 |
| 2) | Cetyl dimethicone (sold under the trade name Abil B9801) | 2.0 |
| 3) | Cyclomethicone (sold under the trade designation Silicone Fluid 345 DC) | 7.0 |
| 4) | A mixture of liquid paraffin and poly-ethylene (sold under the trade name Pioneer PLW) | 3.0 |
| 5) | Glycerol sorbitan fatty acid ester (sold under the trade name Arlacel 481) | 3.0 |
| 6) | Isopropyl palmitate | 4.0 |
| 7) | A mixture of silicone copolyol and cyclomethicone (sold under the trade designation Silicone Fluid 3225C) | 11.0 |
| 8) | 1,3-Butylene glycol | 2.0 |
| 9) | Sodium chloride | 1.0 |
| 10) | Titanium dioxide coated in accordance with Example 1 | 5.0 |
| 11) | Purified water | to 100 |

Components 1 to 7 were mixed together at 65°–70° C. and the titanium dioxide (component 10) dispersed into the mixture using a high shear mixer/homogeniser (Silverson). Components 8, 9 and 11 were mixed together and then slowly added to the titanium dioxide mixture with stirring. The resulting mixture was homogenised using a high shear mixer/homogeniser to give a cream.

Comparative Example A

The titanium dioxide (component 10) of the formulation described in Example 21 was replaced, for comparison purposes only, with titanium dioxide coated with aluminium stearate (sold under the trade designation MT100T). The cast sun protection factors measured for Example 21 and Comparative Example A (at 1.5 mg/cm$^2$) were as shown in Table 2.

TABLE 2

| Formulation | Titanium dioxide | Cast Sun Protection Factor |
|---|---|---|
| Example 21 | MT100T - lecithin coated per Example 1 | 9.3 ± 1.9 |
| Comparative Example A | MT100T | 5.4 ± 0.8 |

EXAMPLE 22

| | | % |
|---|---|---|
| 1) | Microcrystalline wax (sold under the trade name Okerin 239) | 2.0 |
| 2) | Silicone copolyol (sold under the trade name Abil WS08) | 5.0 |
| 3) | White soft paraffin (sold under the trade designation MO80 AB & L) | 3.0 |
| 4) | Light liquid paraffin (sold under the trade designation WOM14) | 3.0 |
| 5) | Apricot kernel oil | 0.5 |
| 6) | Cyclomethicone (sold under the trade designation Silicone Fluid 345DC) | 8.0 |
| 7) | Cetyl dimethicone (sold under the trade name Abil B9801) | 1.0 |
| 8) | Glycerin | 5.0 |
| 9) | Sodium chloride | 2.0 |

-continued

| | % |
|---|---|
| 10) Titanium dioxide coated in accordance with Example 1. | 5.0 |
| 11) Purified water | to 100 |

Components 1 to 7 were mixed together and the titanium dioxide (component 10) dispersed into the mixture using a high shear mixer/homogeniser (Silverson). Components 8, 9 and 11 were mixed together and then slowly added to the titanium dioxide mixture with stirring. The resulting mixture was homogenised using a high shear mixer/homogeniser to give a cream.

EXAMPLE 23 AND COMPARATIVE EXAMPLES B AND C

The titanium dioxide (component 10) of the formulation described in Example 22 was replaced by a different concentration of titanium dioxide coated in accordance with Example 1 or, for comparison purposes only, titanium dioxide coated with aluminium stearate (sold under the trade designation MT100T). The concentrations and resultant cast sun protection factors (measured at 1.5 mg/cm$^2$) were as shown in Table 3 (Example 22 included for comparison).

TABLE 3

| Formulation | Titanium dioxide Type | % w/w | Cast Sun Protection Factor |
|---|---|---|---|
| Example 22 | MT100T - lecithin coated per Example 1 | 5 | 11.2 ± 2.5 |
| Comparative Example B | MT100T | 5 | 5.0 ± 0.9 |
| Example 23 | MT100T- lecithin coated per Example 1 | 10 | 13.4 ± 2.6 |
| Comparative Example C | MT100T | 10 | 8.7 ± 2.7 |

EXAMPLE 24

| | % |
|---|---|
| 1) A mixture of silicone copolyol and cyclomethicone (sold under the trade designation Silicone Fluid 3225C) | 12.0 |
| 2) Cyclomethicone (sold under the trade designation Silicone Fluid 345DC) | 15.0 |
| 3) Cetyl dimethicone (sold under the trade name Abil B9801) | 5.0 |
| 4) Sorbitan sesquioleate (sold under the trade name Arlacel 83) | 3.0 |
| 5) Glycerol sorbitan fatty acid ester (sold under the trade name Arlacel 481) | 0.7 |
| 6) Butylated hydroxytoluene | 0.05 |
| 7) Titanium dioxide - see below | 14.0 |
| 8) Sodium citrate | 4.0 |
| 9) Bronopol | 0.02 |
| 10) Sodium dehydroacetate | 0.15 |
| 11) Purified water | to 100 |

A number of different formulation processes were used as described below:

a) Components 1 to 6 were mixed together at 65°–70° C. and titanium dioxide (component 7) coated in accordance with Example 1 was dispersed into the mixture using a high shear mixer/homogeniser (Silverson). Components 8 to 11 were mixed together and then slowly added to the titanium dioxide mixture with stirring. The resulting mixture was homogenised using a high shear mixer/homogeniser to give a cream.

b) Components 1 to 6 were melted together at 65°–70° C. with lecithin (sold under the trade name P Centrolex) (0.21%). Titanium dioxide coated with aluminium stearate (sold under the trade designation MT100T) was dispersed into the mixture using a Torrance blender. The resultant mixture was homogenised using the Torrance blender. Components 8 to 11 were mixed together and then slowly added to the titanium dioxide dispersion. The resulting mixture was homogenised using a high shear mixer/homogeniser (Silverson) to give a cream.

c) Components 1 to 6 were melted together at 65°–70° C. Titanium dioxide coated with aluminium stearate (sold under the trade designation MT100T) and lecithin (sold under the trade name P Centrolex) (0.21%) were added to a portion of the pre-mixed oil phase to give a mixture containing 40% by weight of titanium dioxide. This mixture was evenly dispersed using a Torrance blender. The remainder of the oil phase was then blended into the titanium dioxide mixture (using a Torrance blender) followed by the slow addition of components 8 to 11. Finally, the mixture was homogenised using a high shear mixer/homogeniser (Silverson) to give a cream.

d) Components 1 to 6 were melted together at 65°–70° C. Titanium dioxide coated with aluminium stearate (sold under the trade designation MT100T) and lecithin (sold under the trade name P Centrolex) (0.21%) were added to a portion of the pre-mixed oil phase to give a mixture containing 40% by weight of titanium dioxide. This mixture was evenly dispersed using a Diosna mixer. The remainder of the oil phase was then blended into the titanium dioxide mixture (using a Diosna mixer) followed by the slow addition of components 8 to 11. Finally, the mixture was homogenised using a high shear mixer/homogeniser (Silverson) to give a cream.

Visual examination (for opacity) and microscopic examination (for agglomeration) of the formulations prepared by methods (a), (b), (c) and (d) after equilibration for at least 48 hours showed no significant differences in the dispersion of titanium dioxide.

Stability of the formulation prepared as described in Example 24(a) was determined by visual examination (for opacity) and microscopic examination (for agglomeration) after equilibration for at least 48 hours and after storage at ambient temperature for 6 months and 12 months. The cast sun protection factor of the product (at 1.5 mg/cm$^2$) after storage for these time intervals was also determined. The results obtained are indicated in Table 4 below.

TABLE 4

| Storage time | Dispersion - estimated from visual and microscopic examinations | Cast Sun Protection Factor |
|---|---|---|
| 48 hrs–1 week | Excellent | 25.5 ± 9.5 |
| 6 months | Excellent | 24.2 ± 9.9 |
| 12 months | Excellent | 27.5 ± 6.7 |

EXAMPLES 25 AND 26 AND COMPARATIVE EXAMPLES D AND E

Titanium dioxide (component 7) of the formulation described in Example 24 was replaced by different concentrations of titanium dioxide coated in accordance with Example 1 or, for comparison purposes only, titanium dioxide coated with aluminium stearate (sold under the trade designation MT100T) and formulated using process (a). The concentrations and resultant cast sun protection factors were as shown in Table 5.

TABLE 5

| Formulation | Titanium dioxide Type | % | Cast Sun w/w Protection Factor |
|---|---|---|---|
| Example 25 | MT100T - lecithin coated per Example 1 | 10 | 24.7 ± 5.8* |
| Comparative Example D | MT100T | 10 | 12.3 ± 2.3* |
| Example 26 | MT100T - lecithin coated per Example 1 | 15 | 28.4 ± 7.8** |
| Comparative Example E | MT100T | 15 | 18.9 ± 4.3** |

*2 mg/cm$^2$
**1.5 mg/cm$^2$

EXAMPLES 27–32

Titanium dioxide particles coated in accordance with Examples 8 to 13 were formulated as described in Example 25 to give the compositions of Examples 27 to 32 respectively. The cast sun protection factors (measured at 2 mg/cm$^2$) were as shown in Table 6 (Example 25 and Comparative Example D included for comparison).

TABLE 6

| Example | Phospholipid | Cast Sun Protection Factor |
|---|---|---|
| D | None | 12.3 ± 2.3 |
| 25 | Lecithin | 24.7 ± 5.8 |
| 27 | Phosphatidyl inositol | 37.0 ± 12.9 |
| 28 | Phosphatidyl ethanolamine | 33.7 ± 8.2 |
| 29 | Phosphatidyl serine | 25.6 ± 4.9 |
| 30 | Hydroxylated lecithin | 35.5 ± 8.7 |
| 31 | Synthetic - derived from rapeseed oil | 29.8 ± 6.7 |
| 32 | Synthetic - derived from soyabean oil | 32.3 ± 8.6 |

EXAMPLE 33

| | % |
|---|---|
| 1) Sorbitan monoisostearate (sold under the trade name Crill 6) | 3.0 |
| 2) A mixture of isopropyl myristate, stearalkonium hectorite and propylene glycol (sold under the trade name Bentone Gel IPM) | 5.0 |
| 3) Cetyl dimethicone (sold under the trade name Abil B9801) | 2.0 |
| 4) Glycerol sorbitan fatty acid ester (sold under the trade name Arlacel 481) | 2.0 |
| 5) Light liquid paraffin (sold under the trade designation WOM14) | 3.0 |
| 6) Isopropyl palmitate | 10.0 |
| 7) Butylated hydroxytoluene | 0.02 |
| 8) Cyclomethicone (sold under the trade designation Silicone Fluid 345DC) | 5.0 |
| 9) Titanium dioxide coated in accordance with Example 1 | 2.5 |
| 10) 1,3-Butylene glycol | 3.0 |
| 11) Magnesium sulphate | 1.0 |
| 12) D-Panthenol | 2.0 |
| 13) Bronopol | 0.02 |
| 14) 20% solution of polyhexamethylene-biguanide hydrochloride (sold under the trade name Arlagard E) | 0.5 |
| 15) Purified water | to 100 |

Components 1 to 8 were mixed together at 65°–70° C. and the titanium dioxide (component 9) dispersed into the mixture using a high shear mixer/homogeniser (Silverson). Components 10 to 15 were mixed together and then slowly added to the titanium dioxide mixture with stirring. The resulting mixture was homogenised using a high shear mixer/homogeniser to give a cream.

EXAMPLE 34

| | % |
|---|---|
| 1) Polyoxyethylene stearyl ether (sold under the trade name Brij 76) | 3.0 |
| 2) Polyoxyethylene stearyl ether (sold under the trade name Brij 72) | 1.5 |
| 3) Dimethicone (sold under the trade designation Silicone Fluid F111/300) | 3.0 |
| 4) Isopropyl myristate | 3.0 |
| 5) Light liquid paraffin (sold under the trade designation WOM14) | 6.15 |
| 6) Glyceryl monostearate (sold under the trade name Cithrol GMS A/S E50743) | 2.0 |
| 7) Stearyl alcohol | 0.5 |
| 8) Capric/Caprylic triglyceride (sold under the trade name Migliol 810) | 4.15 |
| 9) Titanium dioxide coated with aluminium stearate (sold under the trade designation MT100T) | 7.02 |
| 10) Lecithin (sold under the trade name P Centrolex) | 0.28 |
| 11) 20% solution of polyhexamethylene-biguanide hydrochloride (sold under the trade name Arlagard E) | 0.5 |
| 12) Sodium dehydroacetate | 0.15 |
| 13) Purified water | to 100 |

Two different formulation processes were used as described below:
  a) Components 1 to 8 and 10 were melted together at 65°–70° C. Titanium dioxide (component 9) was dispersed into a portion of the pre-mixed oil phase to give a mixture containing 40% by weight of titanium dioxide. This mixture was evenly dispersed using a Torrance blender and then the remainder of the oil phase was blended in. Components 11 to 13 were mixed together at 65°–70° C. and the titanium dioxide dispersion was slowly added using a high shear mixer/homogeniser (Silverson) to give a cream.
  b) Components 1 to 8 were melted together at 65°–70° C. Titanium dioxide (component 9) and lecithin (component 10) were added to a portion of the pre-mixed oil phase to Give a mixture containing 40% by weight of titanium dioxide. This mixture was evenly dispersed using a Diosna mixer and then the remainder of the oil phase was added. Components 11 to 13 were mixed together at 65°–70° C. and the titanium dioxide mixture was slowly added using a high shear mixer/homogeniser (Silverson) to give a cream.

Visual examination (for opacity) and microscopic examination (for agglomeration) of the formulations prepared by methods (a) and (b) after equilibration for at least 48 hours showed no significant differences in the dispersion of titanium dioxide.

EXAMPLE 35

|   |   | % |
|---|---|---|
| 1) | Ethoxylated fatty acid (sold under the trade name Tefose 1500) | 10 |
| 2) | Light liquid paraffin (sold under the trade designation WOM14) | 2 |
| 3) | Ethoxylated triglyceride (sold under the trade name Labrafil M2130CS) | 3 |
| 4) | Stearic acid | 2 |
| 5) | Isopropyl palmitate | 7.5 |
| 6) | Titanium dioxide coated in accordance with Example 1 | 5 |
| 7) | Glycerin | 3 |
| 8) | Purified water | to 100 |

Components 1 to 5 were melted together at 70° C. and the titanium dioxide (component 6) dispersed into the mixture using a high shear mixer/homogeniser (Silverson). Components 7 and 8 were heated to 70° C. The titanium dioxide dispersion was then slowly added to components 7 and 8 using the high shear mixer/homogeniser to give a cream.

We claim:

1. A sunscreen composition which comprises 0.5 to 50% by weight of titanium dioxide particles having a mean primary particle size of less than 100 nm, each of said particles being substantially coated with phospholipid, together with a cosmetically acceptable carrier.

2. A sunscreen composition as claimed in claim 1 wherein the phospholipid is selected from phosphatidyl cholines, phosphatidyl ethanolamines, phosphatidyl serines, phosphatidyl inositols, diphosphatidyl glycerols, sphingomyelins and mixtures thereof.

3. A sunscreen composition as claimed in claim 1 wherein the phospholipid is a synthetic phospholipid or a modified natural phospholipid.

4. A sunscreen composition as claimed in claim 1 wherein the phospholipid carries two $C_{8-32}$ alkyl groups bound to a phosphorylated alcohol.

5. A sunscreen composition as claimed in claim 1 wherein the phospholipid is selected from phosphatidyl cholines, phosphatidyl ethanolamines, phosphatidyl serines, phosphatidyl inositols and mixtures thereof.

6. A sunscreen composition as claimed in claim 1 wherein the phospholipid is lecithin.

7. A sunscreen composition as claimed in claim 1 wherein the ratio of phospholipid to titanium dioxide on a weight:weight basis is in the range of 0.1:100 to 15:100.

8. A sunscreen composition as claimed in claim 13 comprising a water-in-oil emulsion which comprises:
  a) 0.5 to 30% by weight of titanium dioxide particles which have a mean primary particle size of less than 100 nm, each of said particles being substantially coated with phospholipid;
  b) 5 to 50% by weight of an oil phase;
  c) 1 to 15% by weight of an emulsifier; and
  d) at least 40% by weight of an aqueous phase.

9. A sunscreen composition as claimed in claim 8 wherein the phospholipid is selected from phosphatidyl cholines, phosphatidyl ethanolamines, phosphatidyl serines, phosphatidyl inositols, diphosphatidyl glycerols, sphingomyelins and mixtures thereof.

10. A sunscreen composition as claimed in claim 8 wherein the phospholipid is a synthetic phospholipid or a modified natural phospholipid.

11. A sunscreen composition as claimed in claim 8 wherein the phospholipid carries two $C_{8-32}$ alkyl groups bound to a phosphorylated alcohol.

12. A sunscreen composition as claimed in claim 8 wherein the phospholipid is selected from phosphatidyl cholines, phosphatidyl ethanolamines, phosphatidyl serines, phosphatidyl inositols and mixtures thereof.

13. A sunscreen composition as claimed in claim 8 wherein the phospholipid is lecithin.

14. A sunscreen composition as claimed in claim 8 wherein the ratio of phospholipid to titanium dioxide on a weight:weight basis is in the range of 0.1:100 to 15:100.

15. A sunscreen composition as claimed in claim 8 comprising a water-in-oil emulsion which comprises:
  (a) 2.5 to 15% by weight of titanium dioxide particles which have a mean primary particle size of less than 100 nm, each of said particles being substantially coated with phospholipid;
  (b) 10 to 30% by weight of an oil phase;
  (c) 2 to 10% by weight of an emulsifier;
  (d) at least 40% by weight of an aqueous phase.

16. A sunscreen composition as claimed in claim 1 comprising an oil-in-water emulsion which comprises:
  a) 0.5 to 30% by weight of titanium dioxide particles which have a mean primary particle size of less than 100 nm, each of said particles being substantially coated with phospholipid;
  b) 5 to 40% by weight of an oil phase;
  c) 1 to 20% by weight of an emulsifier; and
  d) at least 50% by weight of an aqueous phase.

17. A sunscreen composition as claimed in claim 16 wherein the phospholipid is selected from phosphatidyl cholines, phosphatidyl ethanolamines, phosphatidyl serines, phosphatidyl inositols, diphosphatidyl glycerols, sphingomyelins and mixtures thereof.

18. A sunscreen composition as claimed in claim 16 wherein the phospholipid is a synthetic phospholipid or a modified natural phospholipid.

19. A sunscreen composition as claimed in claim 16 wherein the phospholipid carries two $C_{8-32}$ alkyl groups bound to a phosphorylated alcohol.

20. A sunscreen composition as claimed in claim 16 wherein the phospholipid is selected from phosphatidyl cholines, phosphatidyl ethanolamines, phosphatidyl serines, phosphatidyl inositols and mixtures thereof.

21. A sunscreen composition as claimed in claim 16 wherein the phospholipid is lecithin.

22. A sunscreen composition as claimed in claim 16 wherein the ratio of phospholipid to titanium dioxide on a weight:weight basis is in the range of 0.1:100 to 15:100.

23. A sunscreen composition as claimed in claim 16 comprising an oil-in-water emulsion which comprises:
  (a) 2.5 to 15% by weight of titanium dioxide particles which have a mean primary particle size of less than 100 nm, each of said particles being substantially coated with phospholipid;
  (b) 10 to 20% by weight of an oil phase;
  (c) 2 to 15% by weight of an emulsifier;
  (d) at least 50% by weight of an aqueous phase.

24. A sunscreen composition as claimed in claim 1 which comprises 20 to 50% by weight of titanium dioxide particles which have a mean primary particle size of less than 100 nm, each of said particles being substantially coated with phospholipid in an oil phase dispersion.

* * * * *